(12) United States Patent
Consigny

(10) Patent No.: US 9,433,722 B2
(45) Date of Patent: Sep. 6, 2016

(54) VASCULAR SHIELD AND DELIVERY SYSTEM

(75) Inventor: Paul M. Consigny, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 271 days.

(21) Appl. No.: 13/205,921

(22) Filed: Aug. 9, 2011

(65) Prior Publication Data

US 2013/0041453 A1 Feb. 14, 2013

(51) Int. Cl.
| | | |
|---|---|---|
| *A61F 2/82* | (2013.01) | |
| *A61M 1/36* | (2006.01) | |
| *A61B 17/12* | (2006.01) | |
| *A61B 17/122* | (2006.01) | |
| *A61B 17/08* | (2006.01) | |
| *A61B 17/11* | (2006.01) | |
| *A61B 17/00* | (2006.01) | |

(52) U.S. Cl.
CPC ............. *A61M 1/3655* (2013.01); *A61B 17/08* (2013.01); *A61B 17/12* (2013.01); *A61B 17/122* (2013.01); *A61B 2017/00778* (2013.01); *A61B 2017/1107* (2013.01); *A61F 2/82* (2013.01)

(58) Field of Classification Search
USPC ................................... 600/37; 606/151–158
See application file for complete search history.

(56) References Cited

U.S. PATENT DOCUMENTS

| | | | |
|---|---|---|---|
| 3,726,279 A * | 4/1973 | Barefoot et al. .............. | 606/151 |
| 6,329,386 B1 | 12/2001 | Mollison | |
| 2004/0010303 A1* | 1/2004 | Bolea et al. .................. | 607/118 |
| 2004/0098104 A1* | 5/2004 | Sirhan et al. ................ | 623/1.15 |
| 2004/0186548 A1* | 9/2004 | Scarcello .................... | 623/1.11 |
| 2004/0260384 A1* | 12/2004 | Allen .......................... | 623/1.12 |
| 2005/0266042 A1* | 12/2005 | Tseng ............................ | 424/423 |
| 2006/0052866 A1* | 3/2006 | Gilles et al. ................. | 623/1.51 |
| 2006/0069426 A1* | 3/2006 | Weinberger .................. | 623/1.16 |
| 2008/0058633 A1* | 3/2008 | Boyden et al. .............. | 600/407 |
| 2008/0091263 A1* | 4/2008 | Iyer et al. .................... | 623/1.42 |
| 2008/0092663 A1* | 4/2008 | Corcoran et al. ............. | 73/700 |
| 2008/0119946 A1* | 5/2008 | Nugent et al. ............. | 623/23.72 |
| 2010/0286791 A1* | 11/2010 | Goldsmith ................... | 623/23.7 |
| 2011/0264184 A1* | 10/2011 | Heltai ........................... | 623/1.1 |
| 2011/0288625 A1* | 11/2011 | Morgan et al. .............. | 623/1.11 |

* cited by examiner

*Primary Examiner* — Yashita Sharma
*Assistant Examiner* — Rebecca Preston
(74) *Attorney, Agent, or Firm* — Randy Shen; Blakely, Sokoloff, Taylor & Zafman LLP

(57) ABSTRACT

Devices for providing physical support to vascular regions including vascular regions that may contain an anastomosis region are disclosed. These devices may also deliver therapeutic agents to the vascular region. Methods for using these devices are disclosed, as well.

20 Claims, 4 Drawing Sheets

VASCULAR SHIELD AND DELIVERY SYSTEM

BACKGROUND

Vascular access is important for the treatment of some chronic diseases such as those requiring hemodialysis treatments. A vascular access site should be prepared before starting those kinds of treatments. Doing this allows for easier removal and replacement of the patient's blood during treatment. The access site should allow for continuous, high blood-flow volumes. Common complications from vascular access sites include infection and low blood flow caused by blood clotting in the access passageway.

Arteriovenous (AV) fistulas or AV grafts are basic kinds of vascular access for hemodialysis. An AV fistula connects an artery to a vein in a patient (such as in the patient's forearm) and is useful because it causes the vein to grow larger and stronger allowing easier access to the blood system. The AV fistula is considered the best long-term vascular access for hemodialysis because it provides adequate blood flow, lasts a long time, and has a lower complication rate than other types of access. If an AV fistula cannot be created, an AV graft or venous catheter may be needed.

An AV fistula requires planning because it takes time after surgery to develop—usually several months. But properly formed fistulas are less likely to form clots or become infected than are other access methods. Also, properly formed fistulas may work longer than other kinds of access—sometimes for years.

A synthetic arteriovenous graft is another type of vascular access. It connects an artery to a vein using a synthetic tube, or graft, implanted in the patient's forearm, for example. The graft becomes an artificial vein that can repeatedly receive a needle for blood access during hemodialysis. A graft can be used sooner than an AV fistula—2 or 3 weeks after placement.

Compared with properly formed fistulas, grafts have more clotting and infection problems and need more frequent replacement.

But using vascular grafts as described above changes the circulatory system. The changes caused by the placement of vascular grafts and by the creation of vascular anastomoses or fistulas sometimes cause the circulatory system near the graft, fistula, or anastomosis to develop abnormal shear or circumferential stresses. Moreover, the changes sometimes alter blood pressure, blood flow, and other hemodynamic factors. And the changes can cause torsional stress in the vasculature of or near the graft, fistula, or anastomosis.

What is needed is a device that regulates blood flow and shear stress by limiting the outward expansion of the artery or vein in question, alleviates circumferential wall stress problems, and tethers the affected vessels substantially in place or provides any one or any combination of these benefits.

SUMMARY

The vascular shield according to invention embodiments comprises a body with a wall. The device is adapted to fortify a section of animal vasculature. In some embodiments, the section of vasculature contains an anastomosis.

In these or other embodiments, the phrase "fortify animal vasculature" means that the device prevents or limits outward expansion of the vasculature. In these or other embodiments, "fortify animal vasculature" means to tether a portion of the vasculature substantially in place. In these or other embodiments, "fortify a section of animal vasculature" means that the device substantially limits circumferential wall stress within the vasculature. In some embodiments, "fortify animal vasculature" means that the device prevents or limits outward expansion of the vasculature, tether a portion of the vasculature substantially in place, and substantially limits circumferential wall stress within the vasculature.

Any of these embodiments may relate to a device that comprises portions with substantially tubular or substantially helical shapes. Other shapes function, as well.

Depending on the specific use envisioned for the device, the device may be solid, slitted, perforated, or may comprise a latticework. Some embodiments employ a slitted, tubular structure that comprises a slit extending along the longitudinal axis.

Some embodiments of invention devices are composed of metallic material. Some of these metal-containing embodiments comprise a coating of a polymeric material.

In other embodiments, the device is composed of a polymeric material. In some embodiments, the polymeric material, either structural or coating, comprises a drug-eluting material. The drug-eluting material is chosen such that the drugs treat a variety of ailments. In some embodiments, the drugs treat among other things luminal narrowing, stenosis development, or thrombus formation. In some embodiments, the drug is any one or any combination of anti-proliferative, anti-inflammatory, anti-fibrotic, or anti-thrombotic.

This document also relates to methods comprising implanting a device similar to the devices discussed above.

DETAILED DESCRIPTION

The following description of several embodiments describes nonlimiting examples that further illustrate the invention. All titles of sections contained in this document, including those appearing above, are not to be construed as limitations on the invention, but rather they are provided to structure the illustrative description of the invention that is provided by the specification.

Unless defined otherwise, all technical and scientific terms used in this document have the same meanings as one of ordinary skill in the art to which the disclosed invention pertains commonly understands them to mean. Singular forms—a, an, and the—include plural referents unless the context clearly indicates otherwise. Thus, for example, reference to "fluid" refers to one or more fluids, such as two or more fluids, three or more fluids, etc. When an aspect is said to include a list of components, the list is representative. If the component choice is specifically limited to the list, the disclosure will say so. Moreover, listing components acknowledges that embodiments exist for each of the components and any combination of the components—including combinations that specifically exclude any one or any combination of the listed components. For example, "component A is chosen from A, B, or C" discloses embodiments with A, B, C, AB, AC, BC, and ABC. It also discloses (AB but not C), (AC but not B), and (BC but not A) as embodiments, for example. Combinations that one of ordinary skill in the art knows to be incompatible with each other or with the components' function in the invention are excluded from the invention, in some embodiments.

Figure 1:
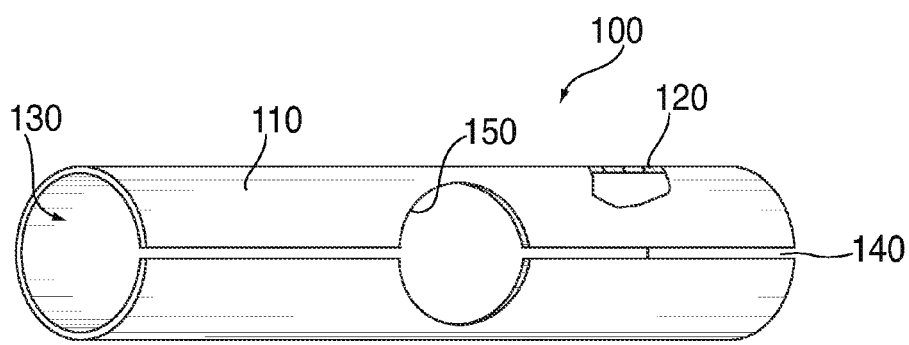
FIG. 1 is a depiction of a vascular shield device according to an embodiment of the invention.

FIG. 1 shows an embodiment of a vascular shield (device) 100. Device 100 has main body 110 with an elongated or tubular shape that is substantially hollow except for walls 120. Passageway, opening, or lumen 130 extends lengthwise through device 100 and through main body 110 forming the tubular shape of device 100. In this embodiment, device 100 has slit 140 situated along the longitudinal axis of device 100 penetrating through wall 120.

Disposed in a side of device 100 is portal 150. In the embodiment shown in FIG. 1, slit 140 intersects portal 150, but other embodiments exist in which this is not so. Depending upon the embodiment, device 100 may have a variety of diameters such as 4 through 8 mm The size and shape of device 100 depend on the size of the target vessel. Device 100 should have a length sufficient to fortify the region of the vessel that needs fortification. The diameter of device 100 should range from slightly smaller to slightly larger than the unfortified vessel region. One goal is to avoid compressing the region to a degree that interferes with the overall function of the vessel. Another goal is to adequately constrain outward expansion or stretching of the vessel.

Depending on the embodiment, portal 150 may have a variety of di-ammeters such as 2 through 8 mm. The diameter of the portal 150 should be large enough to avoid interfering with the vessel branch and small enough so that the trunk vessel receives adequate support near the anastomosis. While the figures depict portal 150 as substantially circular, portal 150 can be any shape that accommodates the branch and fortifies the anastomosis region.

Slit 140 may take a variety of widths. The width may be as narrow as the minimum thickness required to make a slit using whatever fabrication method that has been chosen for device 100. Or the width may be greater. Slit 140 functions to allow device 100 to be temporarily or permanently deformed to aid the surgeon's installation of device 100 around the target vessel or anastomosis. Therefore, the target vessel's identity plays a role in the width of slit 140. In some embodiments, device 100 has a tab or eyelet (not shown) connected along the exterior of device 100. This tab or eyelet may receive one or more sutures when the device is installed on the vasculature to tether or secure device 100 from moving and potentially abrading or otherwise damaging the vasculature or tissue surrounding the vasculature.

For purposes of this disclosure, a device is adapted to fortify a section of animal vasculature when that device has any one or more of the following characteristics or adaptations:

a high enough stiffness to allow the device to resist outward expansion of the vessel wall as blood flow pressurizes the vessel;

a low enough stiffness to prevent undue constriction of the vessel;

construction from material(s) compatible with or not overly toxic to vascular tissue or tissue surrounding vascular tissue;

stability in the body environment on a time scale commensurate with using the device to treat the desired vascular tissue;

a shape to support or fit an intersection of vessels at an anastomosis; or any other characteristic or adaptation that one of ordinary skill in the art would judge as improving the ability of the device to fortify a section of animal vasculature.

For purposes of this disclosure, a device with a size adapted to sheath a section of animal vasculature is a device that has any one or more of the following characteristics or adaptations:

enough length to overlap the desired section of vasculature;

enough width to wrap around the desired section of vasculature;

enough flexibility to deform for installation around the desired section of vasculature; or any other characteristic or adaptation that one of ordinary skill in the art would judge as improving the ability of the device to sheath a section of animal vasculature.

Wall 120 comprises a metallic material optionally coated with a polymeric material. In other embodiments, wall 120 comprises a polymeric material. Thus, wall 120 can be metallic or polymeric in nature. The thickness of wall 120 depends on which materials are selected for the fabrication of device 100. The thickness can range from 25 to 200 microns for metallic walls. For polymeric walls, the thickness can range from 40 to 1000 microns. For wall 120 that is metallic in nature, any polymer coating that does not substantially modify the strength of wall 120 is excluded from the thickness range, in some embodiments.

The thickness of wall 120 and the material of its construction determine the rigidity of device 100. Device 100 should be flexible enough so that a surgeon can permanently or temporarily deform device 100 as the surgeon installs device 100 around a vessel or anastomosis. Device 100 should be rigid enough to provide the desired degree of fortification to the anastomosis region after installation.

Modifications of the material of the device described above and alternative embodiments allowing or providing drug delivery are discussed next. These modifications are equally applicable to the various device embodiments described below.

Metals composing the metallic material of device 100 include anyone or any combination or any alloy of stainless steel; nickel-free stainless steel; 316L stainless steel; high nitrogen stainless steel, e.g., BIODUR108; tantalum; tungsten; molybdenum; silicon; platinum-iridium alloy; molybdenum-rhenium alloy; gold; cobalt-chromium alloy (ELGILOY); cobalt-chromium alloy L-605; cobalt-chromium-tungsten alloys; cobalt-nickel-chromium alloys; cobalt-nickel-chromium-molybdenum alloys; silver; titanium; MP35N; MP20N; nitinol (ELASTINITE); nickel-titanium alloy; nickel-titanium-vanadium alloy; platinum-iridium alloy; or magnesium provided that the metals, combination of metals, or alloys of metals are biocompatible enough that one of ordinary skill in the art would consider them suitable for use in invention metallic materials.

"MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

"Polymer," "poly," and "polymeric" refer to materials resulting from a polymerization reaction and are inclusive of homopolymers and all forms of copolymers. "Copolymers" include random, alternating, block, and graft variations. Also, those of ordinary skill in the art recognize that "terpolymer", or polymers made up of more than three different mers are a subset of copolymers.

Device 100 may be composed of polymers. Representative examples of such polymers include, among others, any one or any combination of fluorinated polymers or copolymers, e.g., poly(vinylidene fluorides), poly(vinylidene fluoride-co-hexafluoro propenes), poly(tetrafluoroethylenes), and expanded poly(tetrafluoroethylenes); poly(propylenes); co-poly(ether-esters); poly(ethylene oxides)/poly(lactic acids); poly(alkylene oxalates); poly(phosphazenes); poly(sulfones); poly(N-vinyl pyrrolidones); poly(ethylene oxides); poly(aminocarbonates); poly(iminocarbonates); poly(anhydride-co-imides); poly(hydroxyvalerates); poly(urethanes); vinyl halide polymers and copolymers, e.g., poly(vinyl chlorides); poly(vinyl ethers), e.g., poly(vinyl methyl ethers); poly(acrylonitriles); poly(vinyl ketones); silicones; poly(esters); poly(olefins); copolymers of poly(isobutylenes); copolymers of ethylene-alphaolefins; poly(L-lactic acids); poly(L-lactides); poly(caprolactones); poly(lactide-co-glycolides); poly(hydroxybutyrates); poly(hydroxybutyrate-co-valerates); poly(dioxanones); poly(orthoesters); poly(anhydrides); poly(glycolic acids); poly(glycolides); poly(D,L-lactic acids); poly(D,L-lactides); poly(glycolic acid-co-trimethylene carbonates); poly(phosphoesters); poly(phosphoester urethanes); poly(vinyl aromatics), e.g., poly(styrenes); poly(lactides); poly(lactide-co-glycolide) copolymers; poly(vinyl esters), e.g., poly(vinyl acetates); copolymers of vinyl monomers and olefins, e.g., poly(ethylene-co-vinyl alcohols) (EVALs); copolymers of acrylonitrile-styrenes; ABS resins; copolymers of ethylene-vinyl acetates; poly(trimethylene carbonates); poly(amides), e.g., Nylon 66 and poly(caprolactams); alkyd resins; poly(carbonates); poly(oxymethylenes); poly(imides); poly(ester amides); poly(ethers) including poly(alkylene glycols), e.g., poly(ethylene glycols) and poly(propylene glycols); epoxy resins; polyurethanes; rayons; rayon-triacetates; biomolecules, e.g., fibrins; fibrinogens; starches; poly(amino acids); peptides; proteins; gelatins; chondroitin sulfates; dermatan sulfates (copolymers of D-glucuronic acids or L-iduronic acids and N-acetyl-D-galactosamines); collagens; hyaluronic acids; and glycosaminoglycans; poly(iminocarbonates); poly(ethylenes); other poly(saccharides), e.g., poly(N-acetylglucosamines); chitins; chitosans; celluloses; cellulose acetates; cellulose butyrates; cellulose acetate butyrates; cellophanes; cellulose nitrates; cellulose propionates; cellulose ethers; carboxymethylcelluloses; or their derivatives, analogs, homologues, congeners, salts, or copolymers.

In some embodiments, the polymers can be biodegradable, bioerodible, or bioabsorbable. Biodegradable, bioerodible, or bioabsorbable polymers include, among others things, any one or any combination of polymers provided that the polymer is biodegradable, bioerodible, or bioabsorbable. In some embodiments, useful mers for these polymers are any one or any combination of, e.g., α-hydroxycarboxylic acids, cyclic diesters of α-hydroxycarboxylic acids, dioxanones, lactones, cyclic carbonates, cyclic oxalates, epoxides, glycols, anhydrides, lactic acids, glycolic acids, lactides, glycolides, ethylene oxides, ethylene glycols, PEGs, alcoholcontaining mers, or other amino-acid-containing mers; poly(esters); poly(ester amides); poly(hydroxyalkanoates) (PHA); poly(caprolactones); poly (lactides); polyp-lactic acids); poly(L-lactic acids); poly(D,L-lactic acids); poly(meso-lactic acids); poly(D-lactide); poly(L-lactide); poly(D,L-lactide); poly(meso-lactide); poly(L-lactide-co-meso-lactide); poly(D-lactide-co-meso-lactide); poly(D,L-lactide-co-meso-lactide); poly(D,L-lactide-co-PEG) block copolymers; poly(D,L-lactide-co-trimethylene carbonate); poly(glycolides); poly(lactide-co-glycolide); poly(dioxanones); poly(anhydrides); poly(glycolic acid-co-trimethylene carbonate); poly(phosphoesters); poly(phosphoester urethanes); poly(amino acids); poly(cyanoacrylates); poly(trimethylene carbonate); poly(carbonates); poly(imino carbonates); poly(urethanes); copoly(ether-esters), e.g. PEO/PLA; poly(alkylene oxalates); poly(phosphazenes); PHA-PEG; poly(glycerol sebacate); tyrosine-derived polycarbonates containing desaminotyrosyl-tyrosine alkyl esters, e.g., desaminotyrosyl-tyrosine ethyl ester (poly(DTE carbonate)); collagens; chitosans; alginate; fibrins; fibrinogen; cellulosics; starches; dextrans; dextrins; hyaluronic acids; heparins; glycosaminoglycans; poly(saccharides); elastins; poly(hydroxyacids); poly(hydroxyalkanoates); poly(orthoesters); poly(oxymethylenes); poly(imides); or any of their derivatives, analogs, homologies, salts, or copolymers.

Polymers for use with this invention as coating polymers should have good adhesion to the surface of implantable devices, such as a metallic surface of a vascular shield. Polymer coatings for vascular shields are selected from, among other polymers, any one or any combination of poly(isocyanates), unsaturated polymers, high amine content polymers, acrylates, polymers with high content of hydrogen bonding groups, silane coupling agents, other biocompatible polymers, or any of their derivatives, analogs, homologues, salts, or copolymers.

Representative examples of polyisocyanates include triisocyanurates, alphatic polyisocyanate resins based on hexamethylene diisocyanates, aromatic polyisocyanate prepolymers based on diphenylmethane diisocyanates, polyisocyanate polyether polyurethanes based on diphenylmethane diisocyanates, polymeric isocyanates based on toluene diisocyanates, poly-methylene polyphenyl isocyanates, polyester polyurethanes, or any of their derivatives, analogs, homologues, salts, or copolymers.

Representative examples of unsaturated polymers include poly(caprolactone diacrylates), poly(ester diacrylates), poly(tetramethylene glycol diacrylates), poly(acrylates) with at least two acrylate groups, poly-acrylated polyurethanes, triacrylates, or any of their derivatives, analogs, homologues, salts, or copolymers.

Representative examples of high amine content polymers include poly(ethyleneamines), poly(allylamines), poly(lysines), or any of their derivatives, analogs, homologues, salts, or copolymers.

Representative examples of with a acrylates include copolymers of ethyl acrylates, methyl acrylates, methacrylic acids, acrylic acids, cyanoacrylates, or any of their derivatives, analogs, homologues, salts, or copolymers.

Representative examples of polymers with a high content of hydrogen bonding groups include poly(ethylene-co-polyvinyl alcohols), epoxy polymers based on the diglycidylethers of bisphenol A's with amine crosslinking agents, epoxy polymers cured by polyols and Lewis acid catalysts, epoxy phenolics, epoxy-polysulfides, ethylene vinyl acetates, melamine formaldehydes, poly-vinyl alcohol-covinyl acetate polymers, resorcinol-formaldehydes, urea-formaldehydes, poly(vinylbutyrals), poly(vinylacetates), alkyd polyester resins, acrylic acid modified ethylene vinyl acetate polymers, methacrylic acid modified ethylene vinyl acetate polymers, acrylic acid modified ethylene acrylate polymers, methacrylic acid modified ethylene acrylate polymers, anhydride modified ethylene acrylate copolymers, anhydride modified ethylene vinyl acetate polymers, or any of their derivatives, analogs, homologues, salts, or copolymers.

Representative examples of other biocompatible polymers include poly(hydroxyvalerates); poly(L-lactic acids); poly(caprolactones); poly(lactide-co-glycolides); poly(hydroxybutyrates); poly(hydroxybutyrate-co-valerates); poly(dioxanones); poly(orthoesters); poly(anhydrides); poly(glycolic acids); poly(D,L-lactic acids); poly(glycolic acid-co-trimethylene carbonates); poly(phosphoesters); poly(phosphoester urethanes); poly(amino acids); cyanoacrylates); poly(trimethylene carbonates); poly(iminocarbonates); co-poly(ether-esters), e.g., PEO/PLA; poly(alkylene oxalates); poly(phosphazenes); biomolecules, e.g., fibrins, fibrinogens, celluloses, starches, collagens, and hyaluronic acids, or any of their derivatives, analogs, homologues, salts, or copolymers. Also, poly(urethanes), silicones, poly(esters), other polymers, or any of their derivatives, analogs, homologues, salts, or copolymers may also be used if they can be dissolved and cured or polymerized on the device. Representative examples of such polymers are polyolefins, poly(isobutylenes) and ethylene-alphaolefin copolymers; acrylic polymers and copolymers; vinyl halide polymers and copolymers, such as polyvinyl chlorides; poly-vinyl ethers), such as polyvinyl methyl ethers; poly(vinylidene halides), such as poly(vinylidene fluoride and poly(vinylidene chlorides); poly(acrylonitriles); polyvinyl ketones); polyvinyl aromatics), such as poly(styrenes); poly-vinyl esters), e.g., polyvinyl acetates); copolymers of vinyl monomers with each other and olefins, such as ethylene-methyl methacrylate copolymers, acrylonitrile-styrene copolymers, ABS resins, and ethylene-vinyl acetate copolymers; poly(amides), such as Nylon 66 and poly(caprolactams); alkyd resins; poly(carbonates); poly(oxymethylenes); poly(imides); poly(ethers); epoxy resins; rayons; rayon-triacetates, celluloses, cellulose acetates, cellulose butyrates; cellulose acetate butyrates; cellophanes; cellulose nitrates; cellulose propionates; cellulose ethers; carboxymethyl celluloses; or any of their derivatives, analogs, homologues, salts or copolymers.

In some embodiments, the polymeric material is selected for its ability to allow drug elution from the material. As such, the drug-eluting polymer composes the device 100 as a structural polymer, is disposed over a structural polymer composing device 100, and is disposed over the metallic material composing device 100.

For purposes of this disclosure, a material that is described as a layer "disposed over" an indicated substrate, e.g., without limitation, a device body or another layer, refers to a relatively thin coating of the material that is applied to part, some, a majority of, or essentially the entire exposed surface of the indicated substrate. "Exposed surface" means the surface of the substrate that, in use, would be in contact with bodily tissues or fluids. But "disposed over" may also refer to the application of the thin layer of material to an intervening layer that has been applied to the substrate. The material in that case would be applied in such a manner that, were the intervening layer not present, the material would cover part, some, a majority of, or essentially the entire exposed surface of the substrate.

For drug elution, the drug or therapeutic agent is supplied in a drug reservoir layer or drug reservoir region of device 100.

For purposes of this disclosure, "drug reservoir layer" or "drug reservoir region" refers either to a layer of one or more therapeutic agents applied with or to a layer of polymer or a blend of polymers. Thus, the polymer-containing layer has one or more therapeutic agents contained within it. A polymeric drug reservoir layer is designed such that, by one mechanism or another, e.g., by elution or by (bio)degradation of the polymer, the therapeutic substance is released from the layer in order to treat some target tissue. For simplicity's sake, therapeutic substance release is called drug elution irrespective of the mechanism of that release. For the purpose of this invention, the drug reservoir layer may act as a rate-controlling layer. In this document, "rate-controlling layer" refers to a polymer layer that controls the release of therapeutic agents or drugs from the device. While any polymer may be used to construct a drug reservoir layer useful with invention devices, some drug reservoir layer embodiments comprise a high-molecular-weight copolymer of lactic acid, L-lactide, D,L-lactide or meso-lactide with e-caprolactone or derivatives of these.

Many biocompatible polymers can be used as drug reservoir or topcoat layers with invention devices. All such polymers are within the scope of this invention. Suitable polymers for use as a drug reservoir coating include, among others, any one or any combination of poly(vinyl acetates); poly(ethylene-co-vinyl acetate); poly(vinyl acetals), e.g., poly(vinyl butyral); poly(meth)acrylates, e.g., poly(methyl methacrylates), poly(ethyl methacrylates), poly(n-propyl methacrylates), poly(iso-propyl methacrylates), poly(n-butyl methacrylate); copolymers of butyl n-methacrylate with nonpolar monomers, e.g., poly(ethyl methacrylate-co-n-butyl methacrylate); poly(iso-butyl methacrylate); poly(methyl acrylate); poly(ethyl acrylate); poly(n-propyl acrylate); poly(iso-propyl acrylate); poly(n-butyl acrylate); poly(iso-butyl acrylate); styrene-butadiene-styrene triblock copolymers; styrene-ethylenelbutylene-styrene triblock copolymers, e.g., KRATON (Shell Oil Co. of Houston, Tex.); styrene-isobutylene-styrene triblock copolymers; parylene C; organosilicon polymers, e.g., ELASTEON; and halogenated, e.g., fluorinated or chlorinated, polymers, e.g., poly(vinyl chloride); poly(vinyl fluorides), poly(vinylidene chlorides), poly(vinylidene fluorides), e.g., KYNAR (Atofina Chemicals, Inc. of Philadelphia, Pa.); poly(hexafluoropropene); poly(vinylidene fluoride-co-hexafluoropropenes), e.g., SOLEF (Solvay S.A. of Brussels, Belgium); poly(ethylene-co-hexafluoropropene); and various grades of amorphous TEFLON, including poly(tetrafluoroethylene) (Du Pont de Nemours & Co. of Wilmington, Del.); poly(L-lactic acid co-L-aspartic acid); poly(D,L-lactic acid co-L-aspartic acid); poly(L-lactic acid); poly(D,L-lactic acid); poly(L-lactic acid-co-ethylene glycol); poly(D,L-lactic acid co-ethylene glycol); poly(ethylene glycol co-butylene terephthalate); or poly(4-hydroxy-L-proline ester); or any of their derivatives, analogs, homologues, salts, or copolymers.

ELASTEON is the trade name of the block copolymer of methylene diphenyl diisocyanate; 1,4-butanediol; poly(hexamethyleneglycol); and a carbinol terminated poly(dimethylsiloxane) (manufactured by Aor-Tech Biomaterials Co. of Chatswood; Australia), poly[trimellityl imido-L-tyrosine co-sebacic acid co-1,3-bis(para-carboxyphenoxy)propane].

The drug reservoir layer comprising these polymers delivers drugs or therapeutic substances or mixtures comprising drugs or therapeutic agents.

Useful drugs for invention embodiments include any drug that can treat a vascular condition or a condition or illness exhibited by an organism that has a vascular anastomosis either a naturally occurring one or one created surgically. Some illnesses exhibited by an organism, such as a human, that has a vascular anastomosis include restenosis, muscular hyperplasia, hyperproliferation, neointimal thickening, collagen degradation, thrombosis, negative remodeling, or pannus formation.

The shield may be designed to elute: (1) agents that inhibit proliferation (everolimus, zotarolimus, paclitaxel) and thereby reduce intimal thickening; (2) agents that promote thickening of the vascular wall (PDGF, bFGF) and thereby reduce wall stress; (3) agents that promote or mimic normal endothelial function (1-arginine or nitric oxide donor); (4) agents that inhibit thrombosis (heparin or prostacyclin); or (5) agents that inhibit the degradation of collagen (tetracycline), etc.

Some embodiments add conventional drugs, such as small, hydrophobic drugs, to polymer coatings or drug reservoirs on invention vascular shields (as discussed in any of the embodiments, above), making them biodegradable drug systems. Some embodiments graft on conventional drugs or mix conventional drugs with the polymer coatings. Polymers can be coated as blends with a variety of biobeneficial polymers. Moreover, they can serve as base or topcoat layers for biobeneficial polymer layers.

The therapeutic agents may also be any moiety capable of contributing to a therapeutic effect, a prophylactic effect, both a therapeutic and prophylactic effect, or other biologically active effect in a mammal. The agent can also have diagnostic properties. The therapeutic agents include, but are not limited to, small molecules, nucleotides, oligonucleotides, polynucleotides, amino acids, oligopeptides, polypeptides, and proteins. In one example, the therapeutic agent inhibits the activity of vascular smooth muscle cells. In another example, the therapeutic agent controls migration or proliferation of smooth muscle cells to inhibit restenosis.

Therapeutic agents include but are not limited to materials comprising any one or any combination of antiproliferatives, antineoplastics, antimitotics, anti-inflammatories, antiplatelets, anticoagulants, antifibrins, antithrombins, antibiotics, antiallergics, antioxidants, and any pro-drugs, metabolites, analogs, homologues, congeners, functional derivatives, structural derivatives, salts or combinations of these. It is to be appreciated that one skilled in the art should recognize that some of the groups, subgroups, and individual bioactive agents might not be used in some embodiments of the present invention.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy.

Antiproliferatives include, for example, actinomycin D, actinomycin IV, actinomycin I1, actinomycin X1, actinomycin C1, and dactinomycin (COS-MEGEN®, Merck & Co., Inc.).

Antineoplastics or antimitotics include, for example, paclitaxel (TAXOL®, Bristol-Myers Squibb Co.), docetaxel (TAXOTERE®, Aventis S. A.), methotrexate, azathioprine, vincristine, vinblastine, fluorouracil, adriamycin, mutamycin, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, functional derivatives, structural derivatives, salts and combinations thereof.

Antiplatelets, anticoagulants, antifibrin, and antithrombins include, for example, aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, functional derivatives, structural derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, functional derivatives, structural derivatives, salts and combinations thereof.

Antiallergic agents include, but are not limited to, pemirolast potassium (ALAMAST®, Santen, Inc.), and any prodrugs, metabolites, analogs, homologues, congeners, functional derivatives, structural derivatives, salts and combinations thereof.

Examples of anti-inflammatory agents including steroidal and non-steroidal anti-inflammatory agents include tacrolimus, dexamethasone, clobetasol, and combinations of these.

Other bioactive agents useful in the present invention include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]-ethyl-rapamycin; tetrazole containing rapamycin analogs such as those described in U.S. Pat. No. 6,329,386; estradiol; clobetasol; idoxifen; tazarotene; alpha interferon; host cells such as epithelial cells; genetically engineered epithelial cells; dexamethasone; and any prodrugs, metabolites, analogs, homologues, congeners, functional derivatives, structural derivatives, salts and combinations thereof.

Free radical scavengers include, but are not limited to, 2,2',6,6-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethylpiperidine-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, functional derivatives, structural derivatives, salts and combinations thereof.

Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, functional derivatives, structural derivatives, salts and combinations thereof. Other therapeutic substances or agents which may be appropriate include imatinib mesylate, pimecrolimus, and midostaurin. Other therapeutic substances or agents which may be appropriate include alpha-interferon, bioactive RGD, and genetically engineered epithelial cells.

The foregoing substances can also be used in the form of pro-drugs or co-drugs thereof. The foregoing substances are listed by way of example and are not meant to be limiting. Other active agents which are currently available or that may be developed in the future are equally applicable.

Dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

For purposes of this disclosure, "pro-healing" refers to a moiety that aids in the healing process at the aneurysm or within the aneurysm. Pro-healing drugs are useful as drugs and are optionally added to the filling material. In some embodiments, pro-healing drugs are materials that promote the controlled proliferation of muscle cells with a normal and physiologically benign composition, useful pro-healing drugs include enzymes, anti-inflammatory agents, antivirals, anticancer drugs, anticoagulant agents, free radical scavengers, steroidal anti-inflammatory agents, non-steroidal anti-inflammatory agents, antibiotics, estradiol, VEGF, an EPC antibody, biorest, nitric oxide donors, super oxide dismutases, endothelial progenitor cells, super oxide dismutases mimics, nitric oxide, 4-amino-2,2,6,6-tetramethyl-piperidine-1-oxyl (4-amino-TEMPO), dexamethasone, clobetasol, aspirin, pro-drugs of these drugs, co-drugs of these drugs. Any compatible combination of pro-healing drug is also suitable for use in this invention.

The polypeptide Arg-Gly-Asp (RGD) has been demonstrated to be a bioactive factor for human endothelial cell attachment and therefore is expected to exhibit prohealing characteristics. In addition to RGD itself, cyclic RGD (cRGD) and RGD mimetics and small molecules capable of binding as does RGD to other adhesion receptors are within the scope of optional filling material components. RGD mimetics can be prepared by modification of RGD or cRGD. Peptide synthesis, including the synthesis of peptide mimetics, is well documented and can be readily achieved using, for example, combinatorial chemistry. Some examples of cRGD or RGD mimetics include V3 antagonists such as I1b/IIIb antagonists, one example of which is Abciximax; XJ 735; anti-3-integrin antibody F11; cRGD; and other sequences such as laminin-derived SIKVAV; laminin-derived YIGSR; KQAGDV; and VAPG.

Useful drugs also include any substance or combination of substances capable of exerting a therapeutic or prophylactic effect in the practice of the present invention as well as having positive pharmacological effects on the expression of the extracellular matrix. The active ingredient can also enhance wound healing in a vascular site or improve the structural and elastic properties of the vascular site.

Growth factors are also useful drugs in this invention. Growth factors include any one or any combination of vasoendothelial growth factor, fibroblast growth factor, hypoxia inducing factor, monocyte chemoattractant protein, lipid factors, vascular endothelial growth factors, fibroblast growth factors, nicotine, platelet derived growth factor, insulin-like growth factor 1, transforming growth factor, hepatocyte growth factor, estrogens, follistatin, proliferin, prostaglandin E1, prostaglandin E2, tumor necrosis factor, interleukin-8, hematopoietic growth factors, erythropoietin, granulocyte-colony stimulating factors, and platelet-derived endothelial growth factor.

Angiogenic substances are growth factors and may be any one or any combination of the following substances, and hormones and genes that encode any one of the following substances: vascular endothelial growth factor, fibroblast growth factors, monocyte chemoattractant proteins, transforming growth factor beta, transforming growth factor alpha, lipid factors, hypoxia-inducible factor 1-alpha, PR39, nicotine, insulin-like growth factors, placental growth factor, hepatocyte growth factor, estrogen, follistatin, proliferin, cytokines, tumor necrosis factor, erythropoietin, granulocyte colony-stimulating factor, granulocyte macrophage colony-stimulating factor, and angiogenic Also, endogenous compounds may be added to these compounds as drugs, see below.

Anti-inflammatory agents may be used as the drug or as part of drug mixture. Suitable anti-inflammatory agents include, without limitation, steroidal anti-inflammatory agents, nonsteroidal anti-inflammatory agents, or combinations of these. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of pro-inflammatory signaling molecules including antibodies to such biological inflammatory signaling molecules.

In one embodiment, the invention device may be formed from a tube by laser cutting the desired pattern into the tube. The device also may be formed by laser cutting a flat polymeric sheet and then rolling the sheet into a tubular device shape and, in some embodiments, providing a longitudinal weld to form the device. Other methods of forming such devices are well known and include chemically etching a flat polymeric sheet and rolling and then welding it to form the device, or coiling a polymeric wire to form the device. The device may be formed by injection molding a thermoplastic or reaction injection molding a thermoset polymeric material. Filaments of a compounded polymer may be extruded or melt spun. These filaments can then be cut, formed into elements, welded closed, and if desired welded together by heat or solvent to form the device. Some embodiments use a mandrel during laser cutting which can mask the inner, but opposite, surface of the device.

Figure 2:
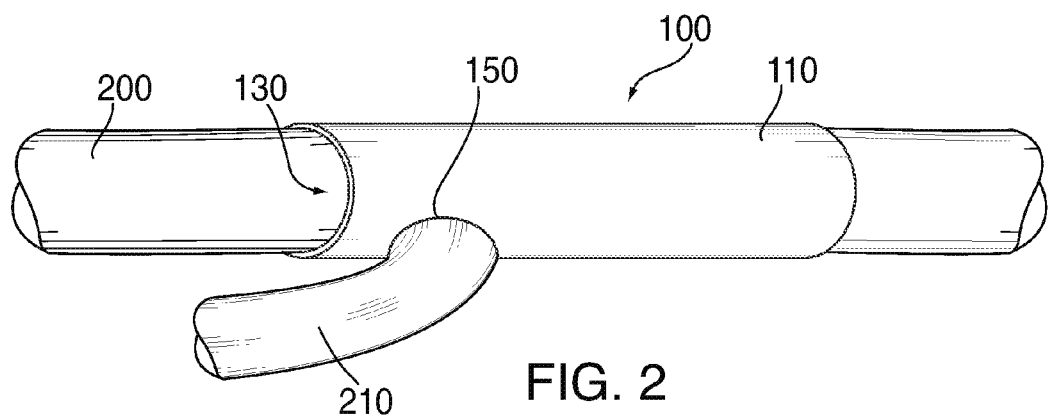
FIG. 2 is a depiction of a vascular shield device installed at a vascular branch.

FIG. 2 shows device 100 as installed onto a branched vessel or anastomosis. Vessel 200 passes through main body 110 through passageway 130 while vessel branch 210 passes through portal 150.

Figure 3:
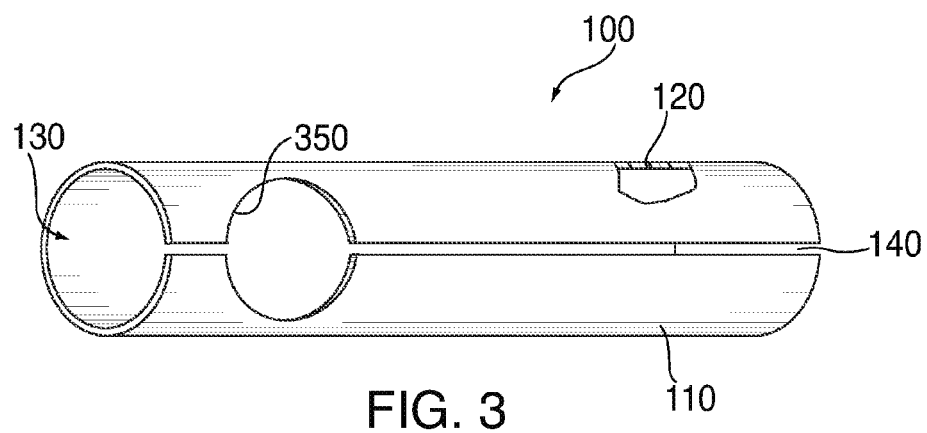
FIG. 3 is an alternative depiction of an embodiment of a vascular shield device.

FIG. 3 shows an alternative embodiment of device 100 of FIG. 1. One difference between the embodiment of FIG. 1 and the embodiment of FIG. 3 is that the embodiment of FIG. 3 has portal 350 situated more closely to the end of main body 110 while FIG. 1 has portal 150 substantially centered along the length of main body 110.

Figure 4:
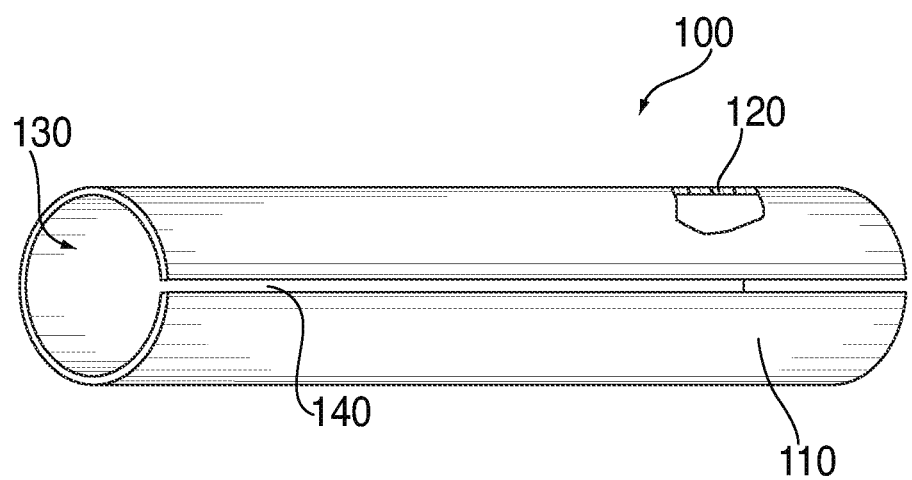
FIG. 4 is an alternative depiction of an embodiment of a vascular shield device.

FIG. 4 shows a vascular shield embodiment in which the main body 110 of device 100 lacks a portal in wall 120.

Figure 5:
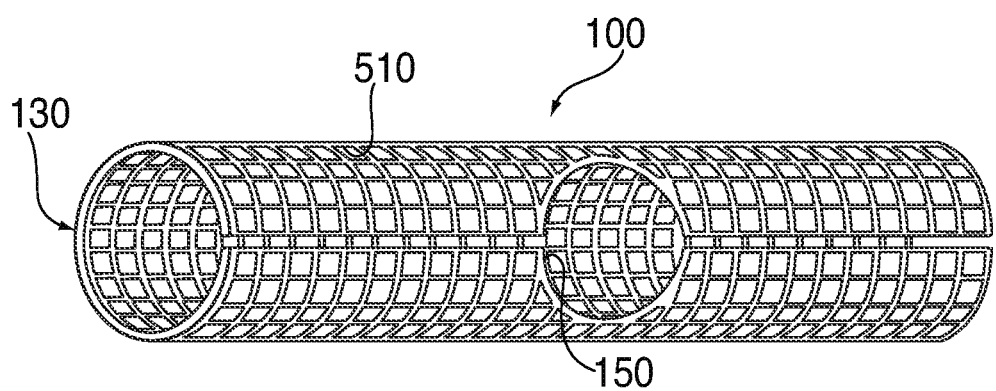
FIG. 5 is an alternative depiction of an embodiment of a vascular shield device in which the wall of the shield is a latticework.

FIG. 5 shows a vascular shield device 100 in which the wall 120 has a series of cutouts 510. These cutouts 510 can be pressed, molded, laser cut, etc. While the embodiment of FIG. 5 shows enough cutouts 510 to create a lattice of wall(s) 120, not all embodiments with cutouts 510 need have such a lattice. Some embodiments have one or more cutouts 510.

Figure 6:
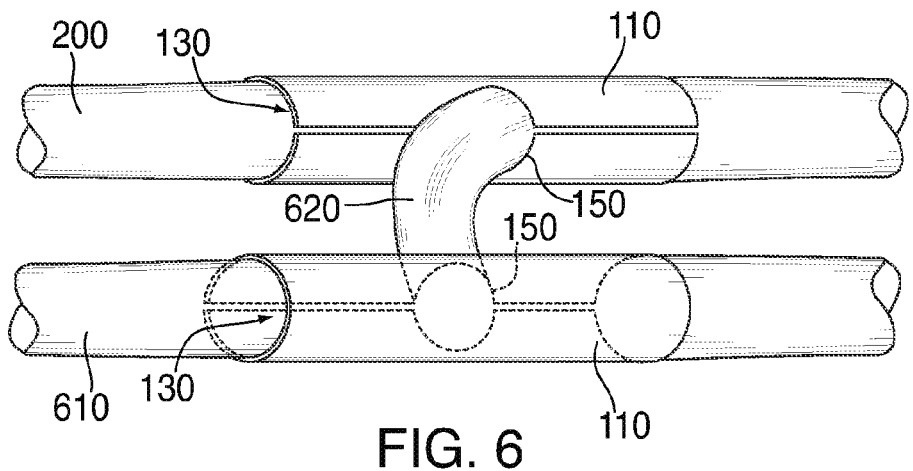
FIG. 6 is a depiction of two devices installed on a graft.

FIG. 6 shows a vascular shield device 100 installed on the prototypical arteriovenous (AV) shunt, graft, or fistula 620. This shunt, graft, or fistula 620, sometimes referred to simply as a shunt, can be autogenous or synthetic. The shunt 620 creates a vascular passageway between artery 200 and another vessel 610, such as an artery or vein.

Figure 7:
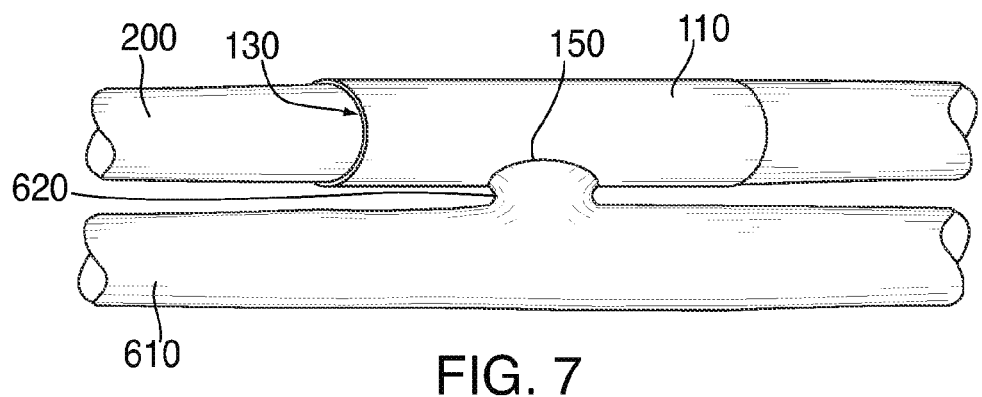
FIG. 7 is depiction of a device installed on an alternative graft.

FIG. 7 shows an arteriovenous shunt that is shorter than the shunt 620 shown in FIG. 6. One vascular shield device is shown installed on artery 200 with artery 200 passing through main body 110 of device 100. Portal 150 accommodate shunt 620. Some embodiments included device 100 with the slit (not shown) dispose lengthwise along the device 100 to penetrate wall 120 of main body 110.

Figure 8:
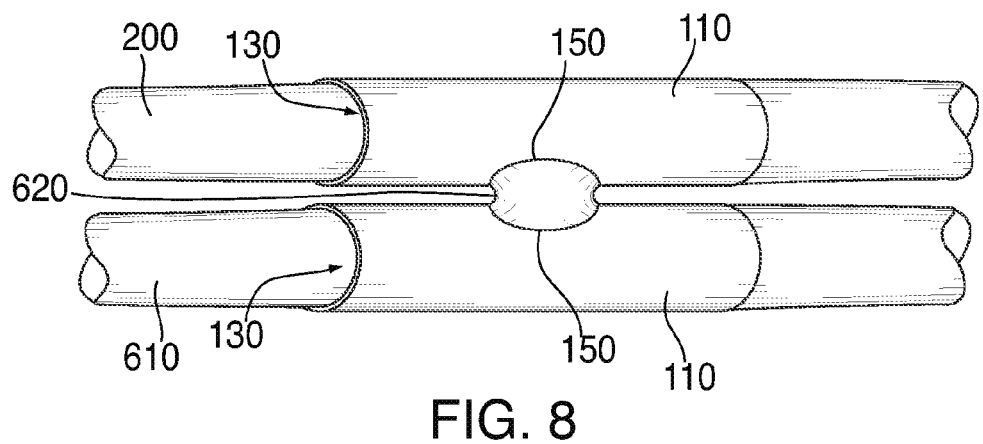
FIG. 8 is a depiction of two devices installed on an alternative graft.

FIG. 8 shows an AV shunt, graft, or fistula with two vascular shield devices 100 installed. One device 100 is shown installed on artery 200 with artery 200 passing through main body 110 of device 100. The second device 100 is shown installed on vessel 610 with vessel 610 passing through main body 110 of device 100. Some embodiments include a slit that is not shown.

Figure 9:
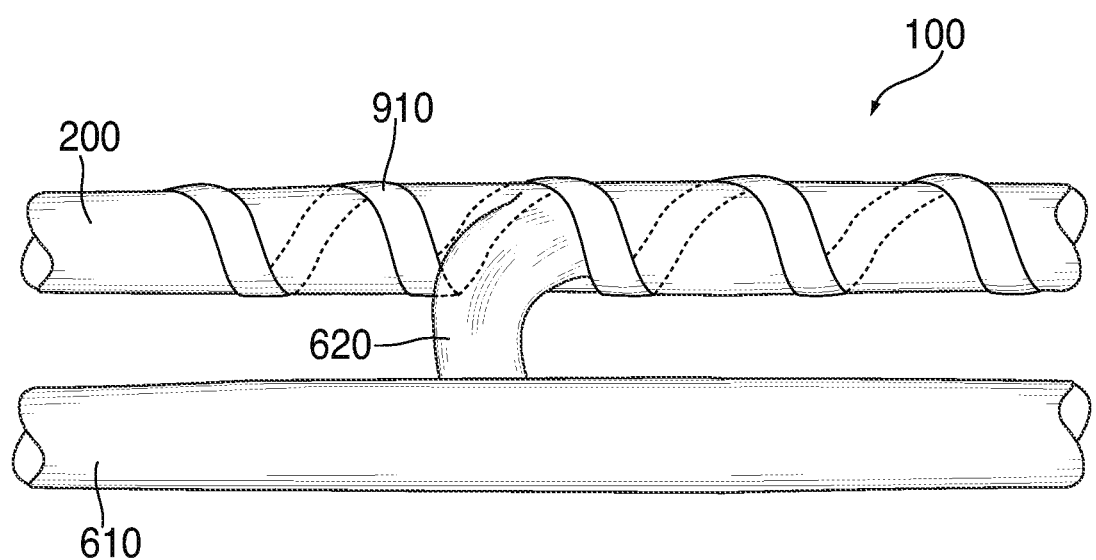
FIG. 9 is an alternative depiction of an embodiment of a vascular shield device.

FIG. 9 shows an alternative embodiment of vascular shield device 100. Main body 910 is a helix comprising a metallic material, optionally with a polymeric material coating, or comprising polymeric material in its entirety.

In operation, device 100 is delivered surgically, laparoscopically, or percutaneously to a vessel in need of fortification. Once there, device 100 is opened along slit 150 and is fitted around vessel 200.

The vessel can be any vessel or vascular structure including a vein, artery, or graft. The vascular structure can be a branch from a vein, artery, or graft. And the vascular structure can be a fistula or shunt either naturally occurring or surgically created. The graft or fistula can be autogenous or synthetic.

The unifying feature is that the area being treated should benefit from some sort of strengthening or fortification. Some such areas include the anastomosis region of the branches, grafts, shunts, or fistulas. But other vascular structures may benefit from such strengthening or fortification with invention devices.

In situations where the vasculature around a vessel branch needs fortification, device 100 is installed onto vessel 200 by opening device 100 along slit 150 and slipping device 100 over vessel 200 such that portal 150 lines up with vessel branch 210. Device 100 is fitted around the vessel 200, portal 150 in device 100 is arranged so that branch 210 passes through portal 150 substantially unhindered.

Branch 210 can already exist or can be formed surgically before installing device 100. The device of FIG. 3 is operated similarly to that of FIG. 1. The FIG. 4 device is installed on an unbranched region of vasculature. Alternatively, it may be used on branched vasculature by installing device 100 adjacent the branch. In operation, device 910 is installed on vessel 200. But instead of being opened along the slit, it is screwed onto vessel 200.

In alternative embodiments, device 100 can be Y-shaped such that branch 210 and the trunk region of the branched vasculature each receive an amount of support or fortification. Alternatively, device 100 can be a helical ribbon that is threaded around the vascular region needing fortification. An appropriate degree of flexibility in the ribbon or adequate space between the ribbon coils allows vessel branch 210 to avoid the ribbon structure much like having portal 150 in wall 120 of the tubular embodiments allows the vessel to avoid the tube material. remain A device made from a biodegradable polymer is intended to remain in the body long enough to accomplish its intended function of, for example, drug delivery. Biodegradable means that a material will breakdown or decompose into harmless compounds as part of a normal biological process. After degradation, erosion, absorption, or resorption has completed, no portion of the biodegradable device, or a biodegradable portion of the device will remain. In some embodiments, negligible traces or residue may be left behind. The duration can range from about a month to a few years, but is typically about six to twelve months.

Biodegradable materials degrade at different rates, ranging from weeks to several years. Consequently, the presence of different biodegradable materials in the device permits the device to degrade as engineered.

In drug-containing embodiments, the drugs may be contained within the biodegradable materials composing the device. In some embodiments, the drugs are within a coating on the device. As the device or coating degrades, drugs release into the surrounding tissue or to the blood stream, or they diffuse through the vessel walls into the blood stream. Thus, the degradation rate of the biodegradable materials controls the drug release rate. A material that degrades rapidly will release the drug faster than a material that degrades slowly.

Additionally, the drug release rate can accelerate or slow down the biodegradable material's degradation rate. Thus, the drug release rate controls the degradation rate.

In another embodiment of the present invention, the polymers and as a as blends that are used to form the device or coatings on the device can be used as a drug delivery reservoir or matrix. To form this matrix, the polymer would be mixed with a therapeutic agent or drug. The therapeutic agent may be present as a liquid, a finely divided solid, or any other appropriate physical form. Typically, but optionally, the matrix will include one or more additives, such as diluents, carriers, excipients, stabilizers, or similar materials.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. Dosage depends on the subject being treated, the severity of the affliction, the judgment of the prescribing physician, etc. Following this or similar procedures, those skilled in the art will be able to prepare a variety of formulations.

The sheath or shield may be constructed of polymer in a way similar to the manner that bioabsorbable or bioresorbable stents are constructed of polymer—laser cut extruded PLA. The design of device 100 depends upon which function is most important—circumferential strength, reabsorption time, flexibility, etc.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

Finally, headings are for the convenience of the reader and do not alter the meaning or content of the disclosure or the scope of the claims.

What is claimed is:

1. A vascular sheath for fortifying a section of vasculature, the sheath comprising:
    a tubular body having a longitudinal axis, a length, and a lumen extending the length of the tubular body, wherein the tubular body includes a wall, and wherein the tubular body includes a stiffness adapted to fortify a section of animal vasculature having pulsatile blood flow, and wherein the stiffness limits expansion of the tubular body from a first configuration to a second configuration when the pulsatile blood flow pressurizes the section of animal vasculature;
    a longitudinal slot through the wall and extending along the longitudinal axis, the longitudinal slot spacing apart a first lateral edge of the wall from a second lateral edge of the wall by a first width when the tubular body is in the first configuration and a second width greater than the first width when the tubular body is in the second configuration; and
    a circular portal in the wall, wherein the longitudinal slot intersects the circular portal, wherein the circular portal includes a first circumference when the tubular body is in the first configuration and a second circumference greater than the first circumference when the tubular body is in the second configuration.

2. The sheath of claim 1, wherein the section of animal vasculature contains an anastomosis.

3. The sheath of claim 2, wherein the wall comprises a region that includes a lattice.

4. The sheath of claim 3, wherein the wall comprises a polymeric material.

5. The sheath of claim 4, wherein the polymeric material comprises a drug eluting material.

6. The sheath of claim 5, wherein the drug eluting material comprises a drug that treats proliferation of vascular cells, neointimal thickening, thrombosis, or collagen degradation.

7. The sheath of claim 6, wherein the drug is any one or any combination of everolimus, zotarolimus, paclitaxel, PDGF, bFGF, 1-arginine, nitric oxide donors, heparin, prostacyclin, tetracycline, antiproliferatives, antineoplastics, antimitotics, anti-inflammatories, antiplatelets, anticoagulants, antifibrins, antithrombins, antibiotics, antiallergics, antioxidants, or any pro-drugs, metabolites, analogs, homologues, congeners, functional derivatives, structural derivatives, or salts.

8. The sheath of claim 5, wherein the drug eluting material comprises a pro-healing drug.

9. The sheath of claim 4, wherein the wall includes a plurality of filaments of the polymeric material.

10. The sheath of claim 4, wherein the polymeric material includes a biodegradable polymer.

11. The sheath of claim 10, wherein the stiffness is based on the biodegradable polymer including one or more of a poly(caprolactone) or a poly(lactide), and wherein the stiffness is further based on the wall having a thickness in a range between 40 to 250 microns.

12. The sheath of claim 11, wherein the poly(lactide) is selected from the group consisting of poly(D-lactic acids), poly(L-lactic acids), poly(D,L-lactic acids), poly(D-lactide), and poly(D,L-lactide).

13. The sheath of claim 3, wherein the wall comprises a metallic material.

14. The sheath of claim 13, wherein the metallic material comprises any one, any combination, or any alloy of stainless steel, nickel-free stainless steel, 316L stainless steel, high nitrogen stainless steel tantalum, tungsten, molybdenum, silicon, platinum-iridium alloy, molybdenum-rhenium alloy, gold, cobalt-chromium alloy, cobalt-chromium alloy L-605, cobalt-chromium-tungsten alloys, cobalt-nickel-chromium alloys, cobalt-nickel-chromium-molybdenum alloys, silver, titanium, MP35N, MP20N, nitinol nickel-titanium alloy, nickel-titanium-vanadium alloy, platinum-iridium alloy, or magnesium.

15. The sheath of claim 14, wherein the metallic material is coated with a polymeric material.

16. The sheath of claim 15, wherein the polymeric material comprises a drug eluting material.

17. The sheath of claim 16, wherein the drug eluting material comprises a drug that is any one or any combination of everolimus, zotarolimus, paclitaxel, PDGF, bFGF, 1-arginine, nitric oxide donors, heparin, prostacyclin, tetracycline, antiproliferatives, antineoplastics, antimitotics, anti-inflammatories, antiplatelets, anticoagulants, anti fibrins, antithrombins, antibiotics, antiallergics, antioxidants, or any pro-drugs, metabolites, analogs, homologues, congeners, functional derivatives, structural derivatives, or salts.

18. The sheath of claim 16, wherein the drug eluting material comprises a pro-healing drug.

19. The sheath of claim 1, wherein the wall has a thickness that ranges from 25 to 1000 microns and the tubular body has an outer diameter that ranges from 4 to 8 mm.

20. The sheath of claim 1, wherein the tubular body includes a first end separated from a second end by the length, and wherein the circular portal is disposed substantially nearer to the first end than to the second end.

* * * * *